United States Patent [19]

Travers et al.

[11] Patent Number: 4,835,129

[45] Date of Patent: May 30, 1989

[54] PROCESS FOR REGENERATING OR ACTIVATING A N-PARAFFIN ISOMERIZATION MORDENITE-CONTAINING CATALYST

[75] Inventors: Christine Travers, Rueil-Malmaison; Jean-Paul Bournonville, Cergy Pontoise; Jean-Pierre Franck, Bougival, all of France

[73] Assignee: Institut Francais du Petrole, Rueil-Malmaison, France

[21] Appl. No.: 164,945

[22] Filed: Mar. 7, 1988

[30] Foreign Application Priority Data

Mar. 6, 1987 [FR] France ............................. 87 03223

[51] Int. Cl.$^4$ ............................................. B01J 38/44
[52] U.S. Cl. ................................... 502/37; 585/739; 585/751
[58] Field of Search ................. 502/37; 585/739, 751

[56] References Cited

U.S. PATENT DOCUMENTS

| | | | |
|---|---|---|---|
| 2,981,694 | 4/1961 | Engel | 502/37 |
| 3,243,384 | 3/1966 | Raarup | 502/37 |
| 3,247,128 | 4/1966 | White et al. | 502/37 |
| 3,647,680 | 3/1972 | Greenwood et al. | 502/37 |
| 3,673,267 | 6/1972 | Chen et al. | 585/739 |
| 3,751,502 | 8/1973 | Hayes et al. | 260/668 A |
| 3,932,554 | 1/1976 | Takase et al. | 252/441 |
| 3,986,982 | 10/1976 | Crowson et al. | 502/37 |
| 3,998,755 | 12/1976 | Hayes et al. | 502/37 |
| 4,232,181 | 11/1980 | Kiovsky et al. | 585/739 |
| 4,657,874 | 4/1987 | Borghard et al. | 502/35 |
| 4,689,312 | 8/1987 | Ngoche et al. | 585/739 |

*Primary Examiner*—Patrick P. Garvin
*Assistant Examiner*—E. D. Irzinski
*Attorney, Agent, or Firm*—Millen & White

[57] ABSTRACT

Process for regenerating or activating a catalyst for isomerizing n-paraffins, containing at least one group VIII metal supported on an acid mordenite, wherein, after having lost at least a part of its initial activity, said catalyst is treated in a first step with an oxygen-containing gas at a temperature lower than about 550° C., so as to remove the major part of the catalyst coke content, and in a second step the resultant product from the first step is oxychlorinated to a temperature of about 200°–500° C. by means of a gas mixture containing oxygen, water and chlorine or at least one chlorinated compound, said chlorine or chlorinated compound being used in a total amount of 0.5–10% by weight, calculated as chlorine, in proportion to the mordenite weight.

18 Claims, No Drawings

PROCESS FOR REGENERATING OR ACTIVATING A N-PARAFFIN ISOMERIZATION MORDENITE-CONTAINING CATALYST

The present invention concerns a process for regenerating moderately or severely deactivated isomerization catalysts comprising at least one group VIII metal supported by at least one mordenite in acid form.

BACKGROUND OF THE INVENTION

The isomerization of normal paraffins of low molecular weight is highly important in the oil industry in view of the particularly high octane number of the isoparaffins formed.

The modification of the regulations in the main industrial countries concerning quality standards of motor gasolines and the progressive cancellation of prior authorizations of using lead-containing additives induce producers to search for improved processes in view to produce lead-free motor gasolines of high octane number.

Processes for converting normal paraffins, having for example 4,5,6 or 7 carbon atoms per molecule, in particular n-paraffins of 5-6 carbon atoms per molecule, to a product containing a high proportion of isoparaffins, are particularly interesting.

By these processes, in particular, the octane number of light gasoline fractions, such for example as straight-run gasolines or those obtained by catalytic reforming, may be improved.

The mechanism of the hydroisomerization reaction is usually considered as a bifunctional mechanism for which catalysts comprising both acid sites and sites of hydrogenating/dehydrogenating function are preferred.

For about twenty years many papers have mentioned the use, in hydroisomerization processes, of catalysts essentially comprising more or less extensively modified zeolites, particularly mordenites, usually in acid form, associated with at least one metal from group VIII of the periodic classification of elements providing for the hydrogenating/dehydrogenating function.

The catalyst efficiency depends in particular on a good dispersion of the metal on mordenite in acid form. It is desirable to obtain the largest possible metal dispersion onto mordenite, so that a maximum of metal atoms be accessible to the reactants. The size of the metal crystallites must be low, preferably at most 10 Angströms ($10 \times 10^{-10}$ m), and their initial distribution onto the freshly prepared catalyst (i.e. a catalyst which has not been contacted with hydrocarbons under isomerization conditions) must be as homogeneous as possible, mainly after regeneration of the at least partially deactivated catalyst.

In fact, the coke, whose formation is unavoidable during the isomerization reaction, deposits onto the catalyst, thus taking part in the total performance decrease of the catalyst which must then be regenerated so as to extend its total life time.

The conventional catalyst regeneration comprises a step of coke removal by combustion. In said step the catalyst is heated into a more or less diluted oxygen stream at a temperature of about 400°–500° C., so as to burn coke. Care must be taken, during this treatment, to avoid a more or less substantial surface loss of the metal particles, obviously resulting in a corresponding loss of catalyst activity. This sintering of the metal phase is well known in the art. Accordingly, special procedures for regenerating these catalysts have been developed.

A particular way of regenerating a platinum-containing zeolite catalyst is disclosed in U.S. Pat. No. 3,986,982. This regeneration consists of contacting the catalyst, after coke burning, with a gas mixture containing an inert gas, 0.5–20% by volume of oxygen and 5–500 ppm by volume of chlorine, either as chlorine, hydrochloric acid or organic chlorinated compound, then purging the catalyst so as to remove oxygen and residual chlorine, and finally reducing this catalyst under hydrogen stream at a temperature of 200°–600° C.

This method, although resulting in a clear improvement of the catalyst activity, does not provide for a good redispersion of platinum, and consequently does not result in an activity of the regenerated catalyst close to that of the fresh catalyst.

SUMMARY OF THE INVENTION

The present invention has as an object provision of a process for regenerating a catalyst containing at least one group VIII metal supported by a mordenite in acid form having lost at least a part of its initial activity, comprising the steps of:

(a) removing the major part of the coke deposited onto the catalyst during the step of contacting said catalyst with the hydrocarbon charge in isomerization conditions, and (b) oxychlorinating the product obtained in step (a), said oxychlorination being conducted at a temperature of about 200° to 500° C. with a gas mixture containing oxygen, water, chlorine and/or at least one chlorinated compound.

The catalyst regenerated according to the process of the present invention substantially recovers its initial activity.

The present invention has also as an object provision of an isomerization process comprising the steps of:

(1) contacting the isomerization catalyst, containing at least one group VIII metal supported onto mordenite in acid form, with the hydrocarbon charge comprising a high proportion of normal paraffins having for example 4,5,6 or 7 carbon atoms per molecule, particularly 5–6 carbon atoms per molecule, under isomerization conditions, said step being continued until the catalyst has lost at least partly its initial activity, (2) treating the partially deactivated catalyst, as obtained at the end of the first step, with an oxygen-containing gas so as to burn at least a part of the coke deposited onto the catalyst during the first step, (3) subjecting the catalyst, containing no more coke or only a small proportion thereof, to oxychlorination under the conditions above mentioned for step (b) of the regenerating process according to the invention, (4) at least partially reducing the catalyst obtained at the end of the third step, preferably in the presence of hydrogen, and (5) contacting the catalyst obtained at the end of the fourth step with a new hydrocarbon charge, under isomerization conditions.

The described cycle, comprising an isomerization period, a regeneration period, a reduction period and then a new isomerization period, may be repeated several times.

The regeneration process according to the invention is applicable to a catalyst mainly comprising an acid mordenite, usually of the characteristics given hereinafter, supporting at least one group VIII metal, preferably platinum, palladium or nickel and having lost, at least partly, its initial activity.

The catalyst regeneration is usually performed when the catalyst activity, in the conditions initially selected for the isomerization reaction, has been reduced to 50–90%, preferably 50–80%, of the initial activity. Although the process of the invention is also applicable to much more deeply deactivated catalysts, i.e. those having an activity lower than 50% of the initial activity, it is usually desirable, for sake of economy, to regenerate the catalyst before its activity has decreased too substantially. In accordance with the industrial conditions in the site where the isomerization is conducted, those skilled in the art can determine the moment at which the regeneration must preferably be performed.

Mordenite is a natural or synthetic alumino-silicate characterized by a Si/Al atomic ratio generally ranging from 4 to 6, its crystalline structure being formed of $SiO_4$ and $AlO_4$ basic tetrahedron chains generating two types of channels: channels of dodecagonal opening (contour with 12 oxygens) and channels of octogonal opening (contour with 8 oxygens).

The mordenite used as main constituent of the catalyst for isomerizing n-paraffins according to the invention may also consist of a mordenite which has been dealuminated according to the methods of the prior art. The Si/Al atomic ratio of the mordenite is usually from about 5 to about 50. However, mordenites having a higher Si/Al atomic ratio, for example up to 80 or even more, can also be used.

A mordenite of Si/Al atomic ratio from 5 to 30 is preferably used.

The mordenite may be of the large pore type, of spherulite morphology, always synthetic, or a so-called small-pore mordenite, of needle morphology, having "unclogged" channels, as disclosed in European Patent No. 196 965.

The mordenite used as catalyst main constituent may usually adsorb molecules of a kinetic diameter higher than about 6.6 Angströms, such as benzene. Mordenite, either synthetic or natural, is initially in solid form and usually contains 4–6.5% by weight of sodium in proportion to the dry mordenite weight. It is thus necessary to shape it in acid form, by any process known in the art, so as to obtain a mordenite in acid form of sodium content lower than about 0.2% by weight and preferably lower than about 0.1% by weight in proportion to the dry mordenite weight.

By the term mordenite in acid form, it is meant, according to the invention, a mordenite containing less than about 0.2% and preferably less than 0.1% by weight of sodium in proportion to the dry mordenite weight.

Usually the mordenite has a mesh volume $V$ of the elementary mesh from 2.73 to 2.78 cubic nanometers ($nm^3$), preferably from 2.74 to 2.77 $nm^3$, and its benzene adsorption capacity is usually at least 5% and preferably at least 8% in proportion to the dry mordenite weight.

The so-defined mordenite is used to prepare the catalyst, either alone or intimately admixed with a matrix, generally amorphous, for example a wet powder of alumina gel. The mixture is then shaped, for example by extrusion, through a drawing plate.

The mordenite content of the obtained carrier must be higher than about 40, preferably higher than 60% by weight. The mordenite content of the mordenite-and-matrix assembly is about 40–95% by weight, preferably about 60–90% by weight. The shaping step may be performed with other matrices than alumina such for example as silica-alumina, natural clays (e.g. kaolin or bentonite) and alumina-boron oxide, and by another shaping technique than extrusion, such for example as pelletizing, bowl granulation or any other technique of the art.

The group VIII hydrogenating metal is then deposited onto this carrier by any process known in the art for depositing metal onto mordenite. For platinum, a cation exchange process with a platinum tetrammine complex will be used: substantially all the metal will then deposit onto mordenite. It is also possible to introduce the group VIII metal directly onto mordenite before its optional admixture with a matrix.

The cation exchange technique may be used to deposit the metal onto the mordenite powder or onto an already shaped product, with or without ammonium competitor cation. The metal may also be deposited onto extrudates or powder by the so-called dry impregnation technique. The dry product is then generally roasted between 300° and 600° C.

The obtained solid usually contains about 0.05–10% by weight of group VIII metal. For platinum and palladium, the content (by weight) is usually 0.05–1%, preferably about from 0.1 to 0.6%. For nickel the content by weight is generally about 0.1–10%, preferably about 0.2–5%.

This solid can be used as an isomerization catalyst in the process according to the invention. The distribution of the metal crystallites is however not very homogeneous. The crystallite sizes have been measured with a high-resolution electron microscope. The solid or catalyst to be observed by transmission electron microscopy is crushed in an agate mortar, then suspended into ethanol by means of ultrasound. A drop of said suspension is then deposited onto a copper grid covered with a thin film of hole-containing carbon. After a short drying step, the sample is observed by the so-called clear field technique. The metal crystallites of the solid obtained by the above-described process have a size from 30 to 200 Angströms. It is possible to obtain a catalyst with a better dispersion of the metal particles by subjecting said solid to an oxychlorination treatment in the hereinafter-defined conditions.

The oxychlorination treatment comprises contacting the solid with chlorine and/or at least one chlorinated compound in the presence of an oxygen and steam-containing gas, at a temperature from about 200° to 500° C., preferably about 300°–500° C., the total amount of chlorine and/or chlorinated compound being from 0.5 to 10%, preferably 1–5% by weight, calculated as chlorine weight, in proportion to the dry mordenite weight. The chlorinated compound may be either inorganic or organic. As chlorinated organic compound, a chloroalkane is usually preferred.

The mordenite-containing solid may be subjected to oxychlorination, either "ex situ" or "in situ".

By treatment "in situ" it is meant a treatment performed at the top of the one or more zones wherein is conducted the proper isomerization reaction or in one or more zones more or less in direct communication with said isomerization zone.

By treatment "ex situ" it is meant a treatment performed either near the site of the industrial isomerization unit, in a zone not in the immediate vicinity of the isomerization zone, or geographically at a distance from the industrial unit (e.g. at the place where the solid is manufactured).

The oxychlorination treatment usually consists of heating the solid, comprising at least one group VIII metal deposited on acid mordenite, in the presence of an oxygen and steam-containing gas stream, for example moist air or oxygen diluted with an inert gas, the oxygen content of the gas mixture being usually of about 10–50%, preferably about 15–35% by weight and its water content being usually about 0.01–5%, preferably about 0.03–2%, and advantageously 0.05–1%. Heating in the presence of oxygen- and water-containing gas mixture is generally conducted progressively up to the selected temperature. The temperature increases for example at a rate of about 5° C. per minute up to the selected temperature. Then, chlorine ($Cl_2$) or for example a chlorinated compound, hydrochloric acid (HCl) or an organic chlorinated compound such as carbon tetrachloride, di-chloropropane, dichloroethane or chloroform, is introduced into the oxygen and steam gas stream, maintained at the selected temperature.

The chlorine or chlorinated compound feed rate is so determined that the time necessary for introducing the selected chlorine amount be about from 0.5 to 6 hours, preferably about 1.5 to 2 hours. When the chlorine introduction is complete, the catalyst is cooled in the presence of the above-described oxygen and steam-containing gas stream, generally up to room temperature.

The residual chlorine content of the catalyst is usually at most 30–50% of the introduced chlorine weight. At this concentration, chlorine is not detrimental to the mordenite structure: i.e. the mordenite structure is substantially unchanged.

The metal particles are homogeneously distributed onto the catalyst obtained after oxychlorination and the size of the metal crystallites is at most 7 Angströms.

The first step of the regeneration process according to the invention must be preferably performed on a catalyst substantially free of water. When the catalyst to be regenerated originates from a storage zone where at least partially deactivated catalyst has been accumulated, it is preferable, before burning coke with oxygen, to heat the catalyst under inert gas at a temperature of about 150° C. for a sufficient time to remove water, and then to increase the temperature during the coke combustion step. This drying step avoids a more substantial dealumination of mordenite, liable to occur during the coke combustion when the catalyst contains water, if, in spite of precautionary measures, the temperature reaches or exceeds 500° C. The drying time is sufficient to limit the water content to less than about 100 ppm by weight and preferably less than about 50 ppm by weight, in proportion to the catalyst weight. The term inert gas, as used herein, means any gas which does not react with the catalyst, such for example as nitrogen, helium, argon or mixtures of said gases.

The first step of removing the major part of the coke contained in the catalyst is performed by contacting the catalyst with an oxygen-containing gas and progressively increasing the temperature until an exothermic combustion reaction or coke burning takes place, usually between 300° and 500° C. This combustion is conducted with care and the operating conditions are preferably so adjusted that the temperature be at most 550° C., preferably at most 500° C. During said combustion step, the major part of the coke is burnt so that the residual coke content by weight of the catalyst is generally lower than 20% and preferably lower than about 10% of the catalyst coke content before combustion (i.e. before at least 80%, preferably at least 90%, of the coke be burnt). In the combustion step, the oxygen-containing gas is usually a mixture of oxygen and inert gas, generally containing 0.1–30%, preferably 0.2–10% by weight of oxygen, such for example as air or air diluted with an inert gas. The oxygen proportion of the combustion-sustaining gas may also depend on the development of the combustion exothermic reaction.

In a preferred embodiment of the coke combustion step, the oxygen-containing gas stream, which is contacted with the catalyst, will further contain chlorine and/or at least one chlorinated compound. By using chlorine and/or a chlorinated compound, the carrier acidity can be maintained and the metal phase sintering reduced. Chlorine and/or the chlorinated compound such for example as hydrochloric acid (HCl) or an organic compound such as carbon tetrachloride, dichloropropane, dichloroethane or chloroform is used in a total amount of 0.1–5%, preferably 0.2–3% by weight, calculated as chlorine weight, in proportion to the catalyst dry mordenite weight content.

The catalyst, after coke burning, is preferably placed in an inert gas stream, then subjected to the second step of the regeneration process according to the invention, optionally after adjustment of the temperature, for example to the desired value for oxychlorination. It is also possible to cool the catalyst, after coke burning, to ordinary temperature and to maintain it in inert gas at said temperature, before subjecting it to oxychlorination, as for example when coke burning and oxychlorination are not performed on the same site.

In spite of the precautionary measures for limiting to a maximum extent the sintering of the metal phase, during coke combustion, the metal particles, observed by electron microscopy, have a considerably increased size. To particle sizes of the freshly prepared catalyst lower than about 7 Angströms(0.7 nm) correspond, after coke burning, particle sizes ranging from about 1 to about 5 nm. With freshly prepared catalyst of particle sizes ranging from about 3 to about 20 nm, particles of very large size, up to 200 nm, may be observed, after the burning step.

The catalyst obtained at the end of the coke combustion step (a) is subjected to oxychlorination under conditions identical to those above-described for oxychlorination of the solid containing mordenite in acid form and at least one group VIII metal.

The oxychlorination treatment is generally performed after the coke combustion step. Although it is also possible to perform combustion and oxychlorination simultaneously, it is generally preferred to be begin with coke combustion, followed with the oxychlorination treatment.

Anyhow, after the oxychlorination step, the metal particles are very homogeneously distributed onto the catalyst and their sizes do not exceed 0.7 nm.

After oxychlorination treatment, the obtained regenerated catalyst is preferably subjected to reduction before being contacted with a new hydrocarbon charge in isomerization conditions. The reduction is generally performed with a gas containing at least one reducing compound, preferably hydrogen. Hydrogen diluted with an inert gas, industrial hydrogen or substantially pure hydrogen (i.e. containing less than 0.5% , preferably less than 0.1% by volume of impurities) can be used. The reduction is usually performed by stages up to a temperature of 350°–750° C., preferably 400°–600° C., for a sufficient time to obtain equal concentrations of reducing compounds at reactor inlet and outlet, thus indicating that the reduction in the selected conditions is complete. This reduction step is preferably performed "in situ".

In the isomerization step, the charge of high light $C_5$-$C_6$ content and hydrogen are contacted with a fresh or regenerated catalyst as above-described, in isomerization conditions. This contact may be performed with a catalyst in fixed bed, in fluidized bed or batchwise.

The isomerization step of the process according to the invention is usually performed at a temperature of 200°-350° C., preferably 230°-300° C. under $H_2$ partial pressures from atmospheric pressure (0.1 MPa) to 7 MPa, preferably from 0.5 to 5 MPa. The space velocity may range from 0.1 to 20 liters, preferably from 1 to 10 liters of liquid hydro-carbons per liter of catalyst and per hour. The $H_2$/charge molar ratio may vary within wide limits and is normally from 0.2 to 20, preferably from 0.5 to 10. The isomerization being a balanced reaction, the isomerizate still contains a high amount of unconverted n-paraffins. These paraffins may be separated from the isomers, for example by distillation or by fractionation over a molecular sieve, and recycled to the isomerization unit.

The treated hydrocarbon cut generally contains at least 80%, preferably at least 90% by weight of n-paraffins having 4, 5, 6 or 7 carbon atoms.

Preferred hydrocarbon cuts are those containing at least 80%, preferably at least 90% of $C_5$ and/or $C_6$ hydrocarbons.

The thermodynamic balance between the different isomers varies considerably with the temperature. Branched hydrocarbons, which have a high octane number are more favored as the temperature is lower. For isomerizing paraffins it is thus desirable to use catalysts which are still active at the lowest possible temperature. The number of moles of 2,2-dimethylbutane(2,2 $DMC_4$), having one of the highest octane numbers among $C_6$ isomers, cannot exceed, at a given temperature, its value at thermodynamic balance: "Chimie des hydrocarbures" by G. Lefebvre, éditions Technip 1978, pages 89-91, and U.S. Pat. No. 4,238,319 (column 1 lines 20-66). The proportion to equilibrium for 2,2 $DMC_4$, in percent, defined as the number of 2,2 $DMC_4$ moles in the reaction effluent (also called collected fraction) multiplied by hundred and divided by the number of 2,2 $DMC_4$ moles at thermodynamic balance at the considered temperature, provides for an easy comparison of the relative activities of the catalysts.

The present invention also concerns a preliminary pretreatment of the isomerization catalyst according to a method inspired by the above-described regeneration process. This pretreatment, in particular, avoids the disadvantages occurring at a later stage after conventional regeneration of the catalysts. In addition, this pretreatment, when combined with regeneration according to the invention, as above-described, gives excellent results.

The process is characterized by the steps of:

(a) contacting said catalyst with a gas containing at least molecular oxygen and 0.01-5% by weight of water at a temperature progressively increased up to 200°-550° C., preferably 300°-550° C. (more particularly 350°-400° C.), (b) continuing said gas supply, at a temperature from 200° to 500° C. (preferably 300°-500° C.), with addition thereto of chlorine or a chlorinated compound so as to introduce into the catalyst a total chlorine amount of 0.5-10% (preferably 1-5%) by weight with respect to the weight of dry mordenite contained in the catalyst, (c) reducing the catalyst obtained in the preceding step by means of a gas containing at least one reducing compound (hydrogen for example), at a temperature from 300° to 750° C. for a sufficient time to obtain substantially the same concentration of reducing compound at the inlet and at the outlet of the catalyst reduction zone.

The isomerization reaction is then performed, for example, by treating said hydrocarbon cut with hydrogen in the presence of the reduced catalyst obtained in the preceding step, at a temperature of about 200°-350° C. under a hydrogen partial pressure from 0.1 to 7 MPa, with a hydrocarbon charge hourly space velocity from 0.1 to 20 $h^{-1}$ and a $H_2$/hydrocarbon charge molar ratio from 0.2 to 20.

The chlorinated compound used in step (b) is selected from the group consisting of hydrochloric acid, carbon tetrachloride, dichloropropane, chloroform and dichloroethane.

The steps (a) and (b) of the process according to the invention may be performed either in two separate zones or in the same zone. Otherwise stated, step (a) may be performed "ex situ" or "in situ".

The pretreatment generally consists of heating the solid, comprising at least one group VIII metal deposited onto acid mordenite, in the presence of a gas stream containing oxygen and steam, for example moist air, or oxygen diluted with an inert gas, the oxygen content of the gas mixture being generally from 10 to 50%, preferably from 15 to 35% by weight, and its water content by weight being generally from 0.01 to 5%, preferably 0.05-1%. Heating in the presence of the oxygen and watercontaining gas mixture is performed progressively up to the selected temperature. Chlorine ($Cl_2$) or a chlorinated compound, hydrochloric acid (HCl) or an organic chlorinated compound such as carbon tetrachloride, dichloropropane, dichloroethane or chloroform is then introduced in the gas stream of oxygen and steam, maintained at the selected temperature.

The chlorine or chlorinated compound feed rate is generally determined so that the time required for introducing the selected chlorine amount be about 1.5-2 hours. After the end of the chlorine introduction the catalyst is cooled, in the presence of the above-described oxygen and steam-containing gas stream, generally to room temperature.

The residual chlorine content of the catalyst is generally at most about 30-50% by weight of the amount of chlorine introduced. At this concentration, chlorine is not detrimental to the mordenite structure: i.e. the mordenite structure remains substantially unchanged.

The distribution of the metal particles onto the catalyst obtained after oxychlorination is homogeneous and the size of the metal crystallites is at most 7 Angströms(0.7 nm).

In the pretreatment, after treatment with chlorine or a chlorinated compound, the obtained catalyst is reduced before being contacted with the hydrocarbon charge in isomerization conditions. The reduction is generally performed by means of a gas containing at least one reducing compound, preferably hydrogen. Hydrogen diluted with an inert gas or substantially pure hydrogen, i.e. containing less than 0.5%, preferably less than 0.1% by volume of impurities, may be used. The reduction is generally conducted by stages up to a temperature from 350° to 750° C., preferably 400°-600° C., for a sufficient time to obtain the same concentration of reducing compounds at the inlet and at the outlet of the reactor, thus indicating the end of the reduction step in the selected conditions. This reduction step is preferably performed "in situ".

EXAMPLES

The following examples are given to illustrate the invention and must not be considered as limiting the scope thereof.

The catalyst performance is defined by the conversion rate (C) of n-hexane, the selectivity (S) to isomerization, the proportion to equilibrium (Pe) of 2,2 dimethylbutane and by the Research octane number (RON).

$$\text{Conversion}(C\ \%) = \frac{\text{input n-hexane weight} - \text{output n-hexane weight}}{\text{input n-hexane weight}} \times 100$$

$$\text{Selectivity}(S\ \%) = \frac{\text{total weight of isomers}}{\text{total weight of the reaction products}} \times 100$$

$$\text{Proportion to equilibrium}(Pe\ \%) = \frac{\text{collected number of 2,2DMC}_4 \text{ moles}}{\text{number of 2,2DMC}_4 \text{ moles at equilibrium}} \times 100$$

EXAMPLE 1

The raw material is a small-pore mordenite referred to as Alite 150, of Société Chimique de la Grande Paroisse. Its chemical formula in anhydrous state is: Na $AlO_2$ $(SiO_2)_{5.5}$, and its benzene adsorption capacity is 1% by weight in proportion to the dry solid weight (mesh volume: 2.79 $nm^3$; sodium content 5.3% (by weight); kinetic diameter of the adsorbed molecules: 0.38 nm). 50g of said powder are dipped into a 2M solution of ammonium nitrate and the suspension is brought to 95° C. for 2 hours.

The ammonium nitrate solution volume is equal to 4 times the weight of dry zeolite (V/W =4). This cation exchange operation is repeated 3 times. After the third exchange, the product is washed with water at 20° C. for 20 minutes with a V/W ratio of 4. The sodium content, expressed in percent by weight with respect to the dry weight, decreases from 5.3 to 0.1%. The product is then filtered and roasted in confined atmosphere (self steaming) at 600° C. for 2 hours.

The product is then subjected to acid etching with 0.58N hydrochloric acid, by bringing it to reflux in the hydrochloric acid aqueous solution at 90° C. for 2 hours with a V/W ratio of 8. The product is then filtered, washed with 0.1N hydrochloric acid and then with water.

The Si/Al atomic ratio of said mordenite is 12, its mesh volume 2.750 $nm^3$, its sodium content 300 ppm and its benzene adsorption capacity 9.6% in proportion to the dry solid weight. This mordenite is shaped as needles of 5 μm average length, having hexagonal faces of about 1 μm length and 0.3 μm height. This modified mordenite is then mixed with a binder of alumina type and the resulting mixture, containing 25% by weight of alumina, is forced through a drawing plate. The obtained extrudates of 1.2 mm diameter are then dried and roasted.

On this carrier, 0.4% of platinum are deposited by cation exchange from tetrammine platinum chloride $Pt(NH_3)_4Cl_2$ with ammonium nitrate as a competitor cation. The sodium content of the final catalyst is 80 ppm. The Si/Al atomic ratio is 12 and the mesh volume 2.750 $nm^3$. The extrudates are then dried and roasted at 500° C. The distribution of the metal particles is relatively heterogeneous and their size ranges from 1 to 20 nm. The obtained catalyst is called catalyst A.

Catalyst A is charged into a fixed bed catalyst unit and reduced under hydrogen in 2-hour stages at 150, 250, 350 and 450° C. It is then tested with a normal hexane charge in the following conditions: temperature of 250° C., pressure of 30 bars, n-hexane weight per mordenite weight and per hour of 2, hydrogen to normal hexane molar ratio of 2. The performance indicated in Table I is obtained after 30 h of catalyst run, then after 12 months of operation. After 12 months of operation, the performance has decreased by about 50%, the catalyst coke content being about 5% by weight. Catalyst A is then subjected to a regeneration treatment according to the following procedure (not conforming with that of the present invention):

A gas mixture containing dry air, nitrogen and chlorine as carbon tetrachloride is introduced into a regeneration reactor containing catalyst A, under atmospheric pressure. The mixture contains 4% by weight of oxygen and 0.3% by weight of chlorine. The temperature is progressively increased up to that of the beginning coke combustion and the gas flow rate is then regulated so that the coke burning temperature remains at about 380° C. The gas mixture supply is continued until the temperature is decreased to 300° C. and the catalyst is then cooled under nitrogen. The obtained catalyst is called catalyst A'. Its coke content is about 0.5% by weight and the Si/Al ratio of its structure is still equal to 12. The particles, as observed by electron microscopy, have a size up to 200 nm.

Catalyst A' is charged into a fixed bed catalyst unit and reduced with hydrogen by 2-hour stages at 150, 250, 350 and 450° C. It is then tested in the same conditions as those above-indicated for catalyst A.

Performance of catalyst A', as indicated in Table I, are obtained after 30 h of run. Catalyst A' did not recover the activity level of fresh catalyst A, but is slightly more active than catalyst A after 12 months of run.

EXAMPLE 2

Another test is conducted with a new charge of catalyst A in the same conditions as those described in example 1. After 12 months of run of catalyst A, it is subjected to a regeneration treatment according to a procedure conforming with the invention, comprising the following operations of:

temperature increase from ordinary temperature up to 400° C. in 1.5 hour under an air stream containing about 1000 ppm by weight of water (0.1%), chlorine injection, as carbon tetrachloride, in moist air maintained at 400° C., so as to introduce 2% by weight of chlorine, in proportion to the mordenite weight contained in the catalyst, in 1.5 hour, progressive decrease to room temperature in a moist air stream (1000 ppm by weight of water).

The obtained catalyst, called catalyst B, is a catalyst A regenerated by the process of the invention.

The electron microscopy analysis of catalyst B shows that all the metal particles have a size smaller than 0.7 nm. The mordenite structure was not changed by the oxychlorination treatment. The catalyst chlorine content is about 0.6% by weight.

Catalyst B is reduced under hydrogen by 2-hour stages at 150, 250, 350 and 450° C. It is then tested in the same conditions as those stated above in example 1 for catalyst A.

Performance of catalyst B, as indicated in Table I, is obtained after 30 h of run. It is observed that catalyst B has recovered the activity level of fresh catalyst A. Moreover, it gives better performance with respect to conversion rate and to production of 2,2 $DMC_4$ than fresh catalyst A.

EXAMPLE 3

Catalyst C is obtained from catalyst A, freshly prepared according to the procedure of example 1.

Catalyst A is charged into the catalyst unit and, before use, is first subjected to a pretreatment comprising the following operations:

temperature increase from ordinary temperature up to 400° C. in 1.5 hour under a stream of moist air containing about 1000 ppm by weight of water, chlorine injection, as carbon tetrachloride, in moist air maintained at 400° C., so as to introduce 2% by weight of chlorine in proportion to the mordenite weight contained in the catalyst, in 1.5 hour, progressive decrease to room temperature under moist air stream (1000 ppm by weight of water).

The obtained catalyst, called catalyst C, is reduced under hydrogen by 2-hour stages at 150, 250, 350 and 450° C., then tested in the same conditions as those stated for catalyst A in example 1.

The performance of catalyst C after 30 hours of run and then after 12 months of operation is indicated in Table II.

After 12 months of operation, the performance of catalyst C is very substantially less reduced as compared with those of non pretreated catalyst. More exactly, catalyst C has the same activity level as catalyst A but is far better than catalyst A, as concerns the conversion and the production of 2,2 $DMC_4$.

Nonetheless, catalyst C is then regenerated according to the procedure described in example 1 for regeneration of catalyst A not conforming with the invention. Regenerated catalyst C is called catalyst C'. Catalyst C' is tested, after reduction in hydrogen by 2-hour stages at 150, 250, 350 and 450° C. in the same conditions as indicated in example 1 for catalyst A. The performance of catalyst C' after 30 hours of run is reported in Table II. The catalyst C' metal particle size vary from 2 to 20 nm.

Another test is conducted with a new charge of catalyst C in the same conditions are those described in example 3. After 12 months of operation, catalyst C is subjected to a regeneration treatment according to the procedure described in example 3. The obtained catalyst C' is charged into a fixed bed catalyst unit, then oxychlorinated according to the procedure described in example 2 for oxychlorinating catalyst A'. The catalyst obtained after oxychlorination is called catalyst D. The catalyst D metal particle size is lower than 0.7 nm.

Catalyst D is reduced, then tested in the conditions stated in example 2 for catalyst B test. The performances of catalyst D after 30 h of run are reported in Table II.

It is observed that comparison catalyst C' does not reach the performances of fresh catalyst C and that catalyst D, regenerated by the process of the invention, gives slightly better performances than those of fresh catalyst C.

TABLE I

| CATALYST | | CONV. % | SELECT. % | Pe % 2,2DMC$_4$ | RON |
|---|---|---|---|---|---|
| A | 30 h | 79.5 | 98.6 | 54.7 | 67 |
|   | 12 months | 35 | 98.6 | 25 | 60 |
| A' (regenerated) | 30 h | 66 | 98.8 | 31.7 | 63 |
| B (regenerated*) | 30 h | 81.2 | 98.2 | 67.0 | 69.6 |
|   | 12 months | 79. | 98.5 | 54.2 | 65.1 |

*according to the invention

TABLE II

| CATALYST | | CONV. % | SELECT. % | Pe % 2,2DMC$_4$ | RON |
|---|---|---|---|---|---|
| C | 30 h | 81 | 98. | 67.0 | 69.6 |
|   | 12 months | 77.4 | 97.9 | 65 | 66.1 |
| C' | 30 h | 79 | 98.0 | 66.8 | 69.5 |
| D | 30 h | 81.3 | 98.3 | 67.2 | 69.6 |
|   | 12 months | 79.7 | 98.6 | 54.9 | 66.2 |

C: activated catalyst A
C': activated and regenerated catalyst A
D: catalyst A activated and regenerated according to the invention.

EXAMPLE 4

In this example, catalyst A is regenerated after 12 months, in the conditions of the invention, as described in example 2.

However, the water content of the air used for the oxychlorination step varies. It is respectively of 50 ppm, 250 ppm and 1000ppm for catalysts B1, B2, B(conforming with example 2) and of 1.5% and 3% respectively for catalysts B3 and B4. These different catalysts are then reduced under hydrogen by 2-hour stages at 150, 250,350 and 450° C. They are then tested in the same conditions as stated in example 1 for catalyst A. The performances of these catalysts after 30 hours of run are reported in table III hereinafter.

TABLE III

| CATALYST | Water Content (ppm) | Conv. % | Select. % | Pe % 2,2DMC$_4$ | RON |
|---|---|---|---|---|---|
| B1 | 50 | 66 | 98.8 | 31.7 | 63 |
| B2 | 250 | 79.1 | 98.6 | 55.2 | 67.2 |
| B | 1000 | 81.2 | 98.2 | 67.0 | 69.6 |
| B3 | 15000 (1.5%) | 78 | 98.5 | 54.2 | 67.0 |
| B4 | 30000 (3%) | 60 | 96.0 | 29.8 | 61.0 |

What is claimed as the invention is:

1. A process for regenerating an isomerization catalyst containing at least one metal from group VIII of the periodic classification of elements, supported by a mordenite in acid form, comprising:
   (a) a first step of removing a major part of catalyst coke content, by combustion with an oxygen-containing gas at a controlled temperature lower than 550° C., and
   (b) a second step wherein the product obtained in step (a) is oxychlorinated at a temperature of about 200°–500° C. by means of a gas mixture containing oxygen, 0.05–1% by weight of water and at least one agent selected from the group consisting of chlorine and chlorinated compounds, the chlorine and/or chlorinated compound amount being a total from 0.5 to 10% by weight, calculated as chlorine weight, in proportion to the dry mordenite weight.

2. A process according to claim 1, wherein the first step of coke removal is conducted so that the temperature remains lower than about 500° C. and the catalyst coke residual content lower than 20% by weight of the catalyst coke content before combustion.

3. A process according to claim 1 wherein the gas used in step (a) for coke combustion contains from 0.1 to 30% by weight of oxygen.

4. A process according to claim 1, wherein the gas used in step (a) for coke combustion further contains chlorine and/or at least one chlorinated compound, in a total amount from 0.1 to 5% by weight, calculated as chlorine weight in proportion to the dry mordenite weight.

5. A process according to claim 1, wherein the isomerization catalyst contains at least one group VIII metal selected from the group consisting of platinum, palladium and nickel, supported by a mordenite in acid form of Si/Al molar ratio from about 5 to about 50 and wherein the mordenite in acid form has a volume V of elementary mesh of 2.73-2.78 nm$^3$, a benzene adsorption capacity higher than 5% by weight in proportion to the dry mordenite weight, and adsorbs molecules of a kinetic diameter higher than about 6.6 Angströms.

6. A process for isomerizing a hydrocarbon cut containing a high proportion of $C_4$ to $C_7$ n-paraffins, comprising:
a first step (a) of contacting said cut, under isomerization conditions, with an isomerization catalyst containing at least one group VIII metal supported by a mordenite in acid form, for a sufficient period to produce a decrease of the catalyst initial activity,
a second step (b) of regenerating the resultant catalyst of reduced activity, said regeneration being performed by the process according to claim 1, and
a third step (c) wherein the regenerating catalyst obtained at the end of step (b) is at least partly reduced and fed back to step (a) for being contacted with a hydrocarbon cut.

7. A process according to claim 6, comprising the steps of:
(a) contacting the catalyst with a gas containing at least molecular oxygen and 0.01-5% by weight of water, at a temperature which is progressively increased up to the range from 200° to 550° C.,
(b) continuing said gas introduction, at a temperature from 200° to 500° C., with addition thereto of chlorine or a chlorinated compound so as to introduce a total amount of 0.5-10% by weight of chlorine, in proportion to the catalyst mordenite weight, into the catalyst,
(c) reducing the catalyst obtained in the preceding step by means of a gas containing at least one reducing compound, at a temperature from 300° to 750° C. for a sufficient time to obtain substantially the same concentration of reducing compound at the inlet and at the outlet of the catalyst reduction zone,
(d) using the reduced catalyst obtained in the preceding step to treat said hydrocarbon cut in the presence of hydrogen, at a temperature from 200° to about 350° C., under a hydrogen partial pressure from 0.1 to 7 MPa, with a hydrocarbon charge hourly space velocity from 0.1 to 20 h$^{-1}$ and a H$_2$/hydrocarbon charge molar ratio from 0.2 to 20.

8. A process according to claim 7, wherein steps (a) and (b) are conducted in two separate zones.

9. A process according to claim 7, wherein steps (a) and (b) are conducted in the same zone.

10. A process according to claim 7, wherein the temperature of step (a) is increased up to 350°-400° C. and wherein, in step (b) chlorine or a chlorinated compound is added so as to introduce into the catalyst 1-5% by weight of chlorine in proportion to the mordenite weight, the chlorinated compound being selected from the group consisting of hydrochloric acid, carbon tetrachloride, dichloropropane, chloroform and dichloroethane.

11. A process according to claim 6, for isomerizing a hydrocarbon cut containing a high proportion of $C_4$ to $C_7$ n-paraffins, in the presence of a catalyst containing at least one group VIII metal supported by at least one acid mordenite of sodium content lower than 0.2% by weight in proportion to the dry mordenite weight, adsorbing molecules of a kinetic diameter higher than 6.6 Angströms, having a mesh volume V of elementary mesh from 2.73 to 2.78 nm$^3$, a benzene adsorption capacity higher than 5% by weight in proportion to the dry mordenite weight, said process being characterized by the steps of:
(a) contacting said catalyst with a gas containing molecular oxygen and 0.01-5% by weight of water at a temperature which is progressively increased up to the range of 200°-550° C., then continuing said gas introduction at a temperature from 200° to 500° C., with addition thereto of chlorine or a chlorinated compound so as to introduce into the catalyst a total amount of 0.5-10% by weight of chlorine, in proportion to the mordenite weight contained in the catalyst,
(b) reducing the catalyst obtained in the preceding step by means of a gas containing at least one reducing compound, at a temperature from 300° to 750° C., for a sufficient time to obtain substantially the same concentration of reducing compound at the inlet and at the outlet of the catalyst reduction zone,
(c) subjecting said hydrocarbon cut, in the presence of hydrogen, to an isomerization reaction in the presence of the reduced catalyst of the preceding step, at a temperature of about 200°-350° C., under a hydrogen partial pressure from 0.1 to 7 MPa, with an hourly space velocity of the hydrocarbon charge from 0.1 to 20 h$^{-1}$ and a H$_2$/hydrocarbon charge molar ratio from 0.2 to 20,
(d) at the end of the isomerization reaction, subjecting at least a part of the catalyst to a combustion by means of an oxygen-containing gas at a controlled temperature lower than 550° C.,
(e) subjecting the resultant catalyst from step (d) to an oxychlorination at a temperature of about 200°-500° C., by means of a gas mixture containing oxygen, water and at least one agent selected from the group consisting of chlorine and chlorinated compounds, used in a total amount of 0.5-10% by weight, calculated as chlorine weight, in proportion to the dry mordenite weight, and
(f) treating with hydrogen and recycling at least a part of the oxychlorinated catalyst to step (c).

12. A process according to claim 11, wherein the temperature in step (a) ranges from 350° to 400° C. and wherein chlorine or a chlorinated compound is then added so as to introduce into the catalyst 1-5% by weight of chlorine, in proportion to the mordenite weight, the chlorinated compound being selected from the group consisting of hydrochloric acid, carbon tetrachloride, chloroform and dichloroethane, and wherein the combustion in step (d) is so conducted that the temperature remains lower than about 500° C.,and the residual coke content of the catalyst after combustion lower than 20% by weight of the catalyst coke content by weight before combustion.

13. A process according to claim 12, wherein the gas used for coke combustion contains 0.1–30% by weight of oxygen and wherein the chlorine or chlorinated compound contained in the gas mixture used for the oxychlorination step (e) amounts to a total of 0.1–5% by weight, calculated as chlorine weight, in proportion to the dry mordenite weight.

14. A process according to claim 1, wherein the catalyst is substantially water-free during combustion in step (a).

15. A process according to claim 14, wherein the catalyst has a water content of less than 100 ppm by weight.

16. A process according to claim 1, wherein the mordenite in acid form has a sodium content of less than 0.2% by weight with respect to dry mordenite.

17. A process according to claim 6, wherein the catalyst is substantially water-free during combustion in step (a).

18. A process according to claim 6, wherein the mordenite in acid form has a sodium content of less than 0.2% by weight with respect to dry mordenite.

* * * * *